US010335142B2

(12) United States Patent
Raybin et al.

(10) Patent No.: US 10,335,142 B2
(45) Date of Patent: Jul. 2, 2019

(54) TWIST NEEDLE PASSER CLOSURE DEVICE

(71) Applicant: BOSTON SCIENTIFIC SCIMED, INC., Maple Grove, MN (US)

(72) Inventors: Samuel Raybin, Marlborough, MA (US); Paul Smith, Smithfield, RI (US); Kevin James McElwee, Franklin, MA (US); John B. Golden, Norton, MA (US); Matthew Robert Jagelski, West Roxbury, MA (US); Ray Hewenson Tong, Foxboro, MA (US); Naroun Suon, Lawrence, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 285 days.

(21) Appl. No.: 15/276,477

(22) Filed: Sep. 26, 2016

(65) Prior Publication Data
US 2017/0086819 A1 Mar. 30, 2017

Related U.S. Application Data

(60) Provisional application No. 62/234,416, filed on Sep. 29, 2015.

(51) Int. Cl.
A61B 17/04 (2006.01)
A61B 17/06 (2006.01)
A61B 17/062 (2006.01)

(52) U.S. Cl.
CPC ...... *A61B 17/0491* (2013.01); *A61B 17/0469* (2013.01); *A61B 17/0625* (2013.01);
(Continued)

(58) Field of Classification Search
CPC . A61B 17/04; A61B 17/0491; A61B 17/0469; A61B 17/06; A61B 17/3496
See application file for complete search history.

(56) References Cited

U.S. PATENT DOCUMENTS

2009/0012538 A1 1/2009 Saliman et al.
2009/0177031 A1 7/2009 Surti et al.
(Continued)

FOREIGN PATENT DOCUMENTS

JP 2012515636 7/2012
JP 2013525083 6/2013

*Primary Examiner* — Vi X Nguyen
(74) *Attorney, Agent, or Firm* — Fay Kaplun & Marcin, LLP

(57) ABSTRACT

A tissue closure device includes a needle and a suture extending therefrom, a proximal head including a proximal slot and a proximal locking mechanism for releasably engaging a first end of the needle in the proximal slot in a first configuration, and a distal head movably coupled to the proximal head so that the proximal and distal heads are movable relative to one another between an open configuration, in which a target tissue is received therebetween, and a closed configuration, in which the target tissue gripped therebetween. The distal head includes a distal slot and a distal locking mechanism for releasably engaging a second end of the needle in the distal slot in a second configuration, the needle movable between the first and second configurations by rotating the needle, the needle alternatingly passed between the proximal and distal heads to thread the suture through the target tissue.

9 Claims, 5 Drawing Sheets

(52) U.S. Cl.
CPC .. *A61B 17/06061* (2013.01); *A61B 17/06066* (2013.01); *A61B 2017/0609* (2013.01); *A61B 2017/06047* (2013.01)

(56) References Cited

U.S. PATENT DOCUMENTS

2012/0277768 A1   11/2012  Viola et al.
2014/0276988 A1    9/2014  Tagge et al.
2014/0296880 A1* 10/2014  Heneveld ........... A61B 17/0469
                                                          606/144

* cited by examiner

TWIST NEEDLE PASSER CLOSURE DEVICE

PRIORITY CLAIM

This application claims priority to U.S. Provisional Patent Application Ser. No. 62/234,416 filed Sep. 29, 2015; the disclosure of which is incorporated herewith by reference.

BACKGROUND

Physicians have been increasingly willing to perform more aggressive interventional and therapeutic endoscopic procedures including, for example, the removal of larger lesions (e.g., cancerous masses), tunneling under the mucosal layer of the gastrointestinal (GI) tract to treat tissue below the mucsoa, full thickness removal of tissue, the treatment of issues of other organs by penetrating and passing out of the GI tract, and the endoscopic treatment/repair of post-surgical issues (e.g., post-surgical leaks, breakdown of surgical staple lines, anastomic leaks). These procedures my increase the risk of perforating the wall of the GI tract, or may require closure of an opening formed in the GI tract wall as part of the procedure. Endoscopic closure can save costs for the hospital and provide benefits to the patient. Conventional devices for tissue closure may be difficult to use and time consuming in certain conditions. In addition, conventional devices may be insufficient to close certain perforations or to treat certain conditions and anatomies such as, for example, large wounds created in the GI tract.

SUMMARY

The present disclosure relates to a tissue closure device, comprising a needle extending longitudinally from a first end to a second end, a suture extending from a distal end attached to the needle to a proximal end extending to a proximal end of the device, a proximal head including a proximal slot extending longitudinally therethrough and a proximal locking mechanism for releasably engaging the first end of the needle in the proximal slot in a first configuration, and a distal head movably coupled to the proximal head so that the proximal and distal heads are movable relative to one another between an open configuration, in which a target tissue is received therebetween, and a closed configuration, in which the target tissue is gripped therebetween. The distal head includes a distal slot extending longitudinally therethrough and a distal locking mechanism for releasably engaging the second end of the needle in the distal slot in a second configuration, the needle movable between the first and second configurations when the proximal and distal heads are in the closed configuration by rotating the needle relative to the proximal and distal heads, the needle alternatingly passed between the proximal and distal heads to thread the suture through the target tissue.

In an embodiment, each of the proximal and distal locking mechanisms may include a pair of diametrically opposed engaging structures.

In an embodiment, the pair of diametrically opposed engaging structures of each of the proximal and distal locking mechanisms may be substantially longitudinally aligned with one another.

In an embodiment, the pair of diametrically opposed engaging features may include protrusions extending into the proximal and distal slots.

In an embodiment, the first end may include a first groove immediately distal of a tapering thereof and a first pair of planar surfaces extending along a portion of the first end so that the first pair of planar surfaces is flush with the first groove, the first groove engagable with the proximal locking mechanism in the first configuration.

In an embodiment, the second end may include a second groove immediately proximal of a tapering of thereof and a second pair of planar surfaces extending along a portion of the second end so that the second pair of planar surfaces is flush with the second groove, the second groove engagable with the distal locking mechanism in the second configuration.

In an embodiment, the first and second pair of planar surfaces may be offset from one another about a longitudinal axis of the needle.

In an embodiment, the distal head and the proximal head may be movably coupled to one another via a connecting element extending proximally therefrom to be slidably received within an opening extending longitudinally through the proximal head.

In an embodiment, the device may further comprise an actuating element for rotating the needle between the first and second configurations, the actuating element including a distal end configured to engage the first end of the needle.

The present disclosure also relates to a system for treating a tissue, comprising an insertion device including a working channel extending therethrough and a closure device sized and shaped to be inserted through the working channel to a target site within a living body. The closure device includes a needle extending longitudinally from a first end to a second end, a suture extending from a distal end attached to the needle to a proximal end extending to a proximal end of the device, a longitudinal member extending from a proximal end to a distal end and including lumen extending therethrough, a proximal head attached to the distal end of the longitudinal member, the proximal head including a proximal slot extending longitudinally therethrough and a proximal locking mechanism for releasably engaging the first end of the needle in the proximal slot in a first configuration, a distal head movably coupled to the proximal head so that the proximal and distal heads are movable relative to one another between an open configuration, in which a target tissue is received therebetween, and a closed configuration, in which the target tissue is gripped therebetween, the distal head including a distal slot extending longitudinally therethrough and a distal locking mechanism for releasably engaging the second end of the needle in the distal slot in a second configuration, and an actuator element for moving the needle between the first and second configurations when the proximal and distal heads are in the closed configuration by rotating the needle relative to the proximal and distal heads, the needle alternatingly passed between the proximal and distal heads to thread the suture through the target tissue.

In an embodiment, each of the proximal and distal locking mechanisms may include a pair of diametrically opposed engaging structures.

In an embodiment, the pair of diametrically opposed engaging structures of each of the proximal and distal locking mechanisms may be substantially longitudinally aligned with one another.

In an embodiment, the pair of diametrically opposed engaging features may include protrusions extending into the proximal and distal slots.

In an embodiment, the first end may include a first groove immediately distal of a tapering thereof and a first pair of planar surfaces extending along a portion of the first end so that the first pair of planar surfaces is flush with the first groove, the first groove engagable with the proximal locking mechanism in the first configuration. The second end may include a second groove immediately proximal of a tapering of thereof and a second pair of planar surfaces extending along a portion of the second end so that the second pair of planar surfaces is flush with the second groove, the second groove engagable with the distal locking mechanism in the second configuration.

In an embodiment, the first and second pair of planar surfaces may be offset from one another about a longitudinal axis of the needle.

The present disclosure also relates to a method for treating a tissue defect, comprising inserting a device to a target area within a patient body via a working channel of an insertion device, positioning the device so that a first target tissue about a periphery of a tissue defect to be treated is received between a distal head and a proximal head of the device, a first end of a needle releasably locked within a proximal slot in the proximal head via a proximal locking mechanism, moving the distal and proximal heads longitudinally toward one another such that a second end of the needle pierces the first target tissue and the second end of the needle is received within a distal slot extending through the distal head, rotating the needle relative to the proximal head so that the first end of the needle is unlocked from the proximal head and the second end of the needle is releasably locked within the distal slot via the distal locking mechanism, and moving the distal and proximal heads longitudinally away from one another such that the needle extends through the first target tissue, threading a suture attached to the needle through the first target tissue.

BRIEF DESCRIPTION

DETAILED DESCRIPTION

Figure 1:
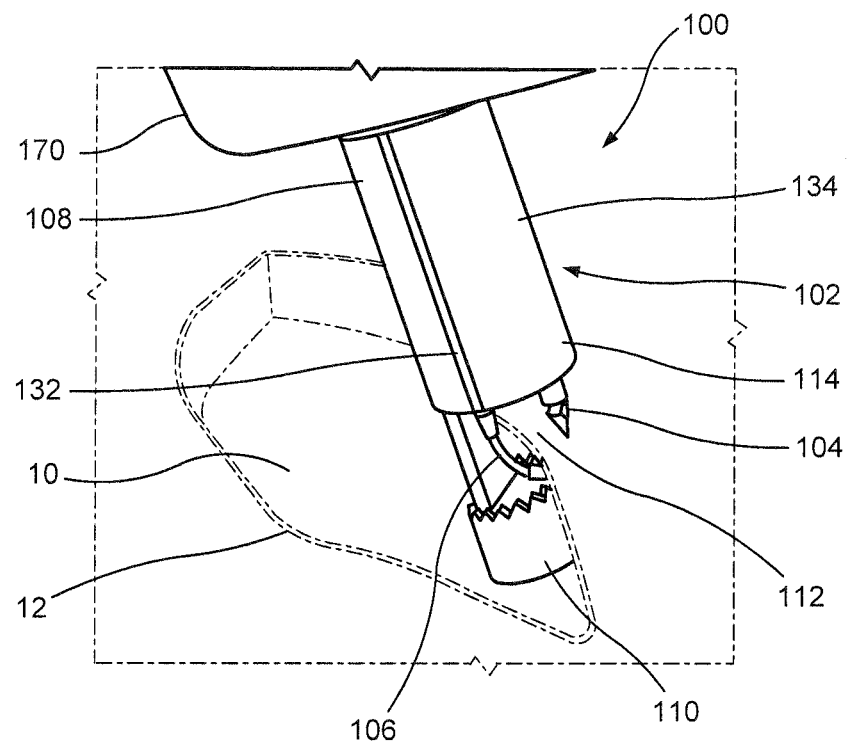
FIG. 1 shows a perspective view of a system according to an exemplary embodiment.

The present disclosure may be further understood with reference to the following description and the appended drawings, wherein like elements are referred to with the same reference numerals. The present disclosure is directed to devices for the treatment of tissue and, in particular endoscopic tissue treatment devices. Exemplary embodiments of the present disclosure describe a system for passing a needle and suture through target tissue between proximal and distal heads of a device to treat a tissue defect such as, for example, a tissue opening. In particular, the needle is passed longitudinally through the target tissue alternatingly between proximal and distal heads of the device to be threaded along about a periphery of the tissue defect. The needle is alternatingly locked to the proximal and distal heads by rotating the needle relative thereto. Once the needle and suture have been threaded about the entire tissue defect in a desired pattern, the suture may be tensioned to cinch the tissue defect to a closed configuration. It should be noted that the terms "proximal" and "distal" are intended to refer to a direction toward (proximal) and away from (distal) a user of the device.

Figure 2:
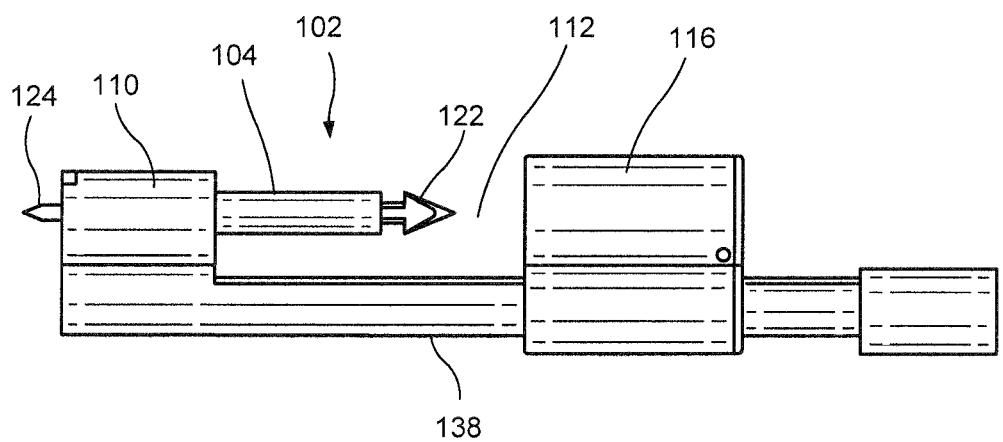
FIG. 2 shows a longitudinal side view of a device according to the system of FIG. 1.
Figure 3:
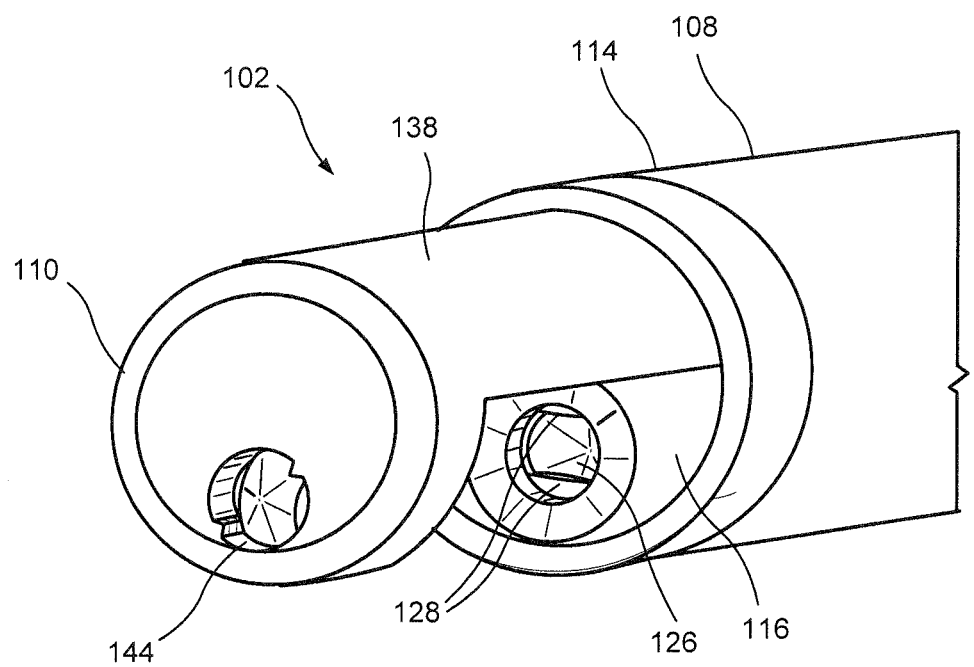
FIG. 3 shows a perspective view of the device of FIG. 1.
Figure 4:
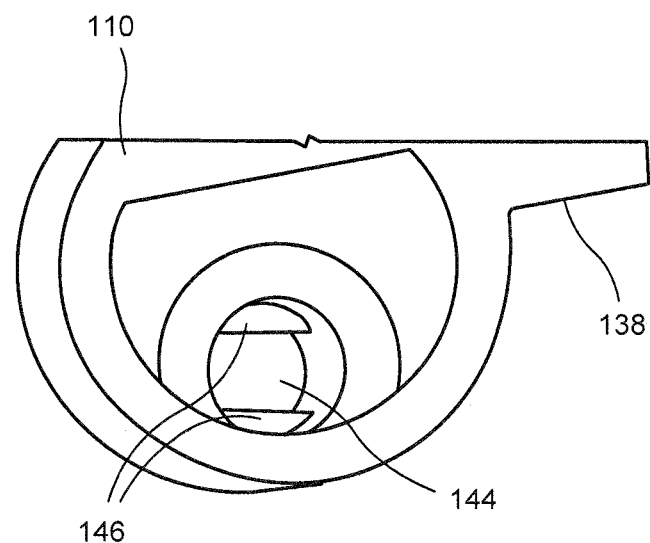
FIG. 4 shows a perspective view of a portion of the device of FIG. 1.
Figure 5:
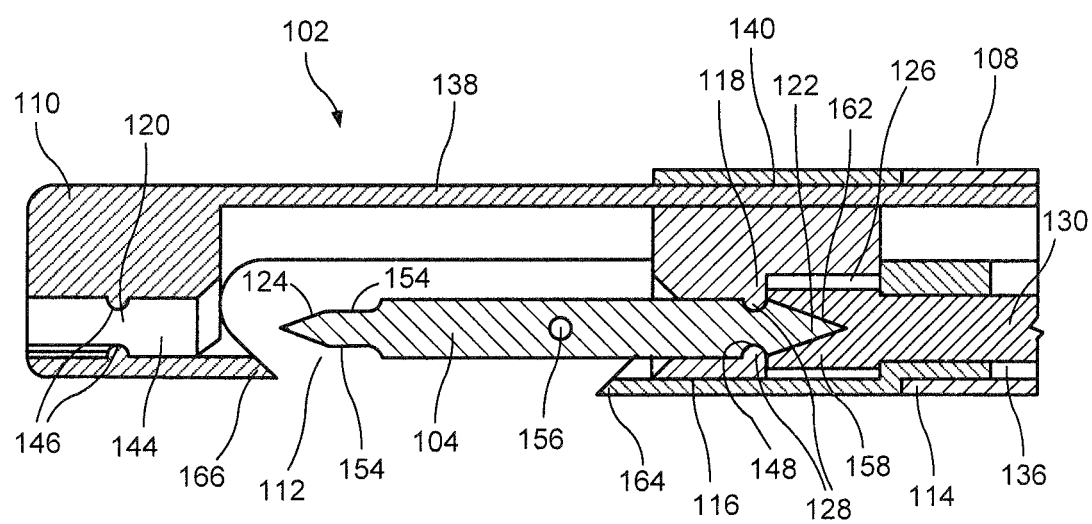
FIG. 5 shows a longitudinal cross-sectional view of the device of FIG. 1, in an open configuration with a needle locked via a proximal locking mechanism.
Figure 6:
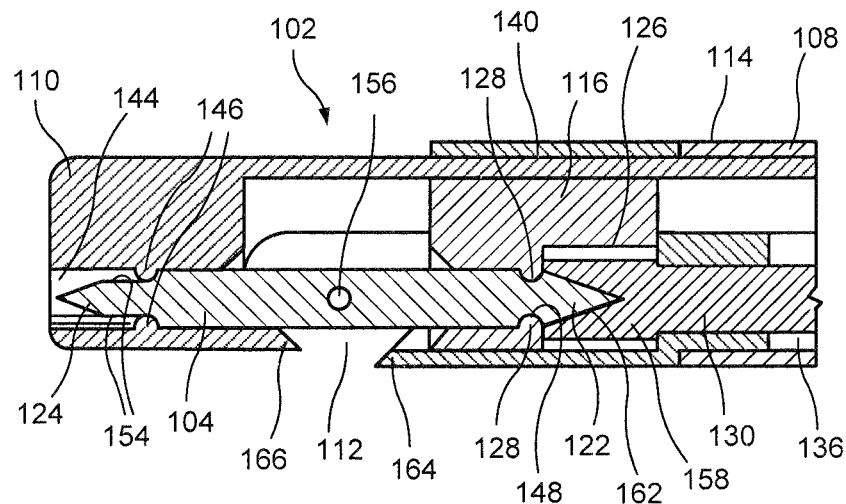
FIG. 6 shows a longitudinal cross-sectional view of the device of FIG. 1, in a closed configuration with the needle locked via the proximal locking mechanism.
Figure 7:
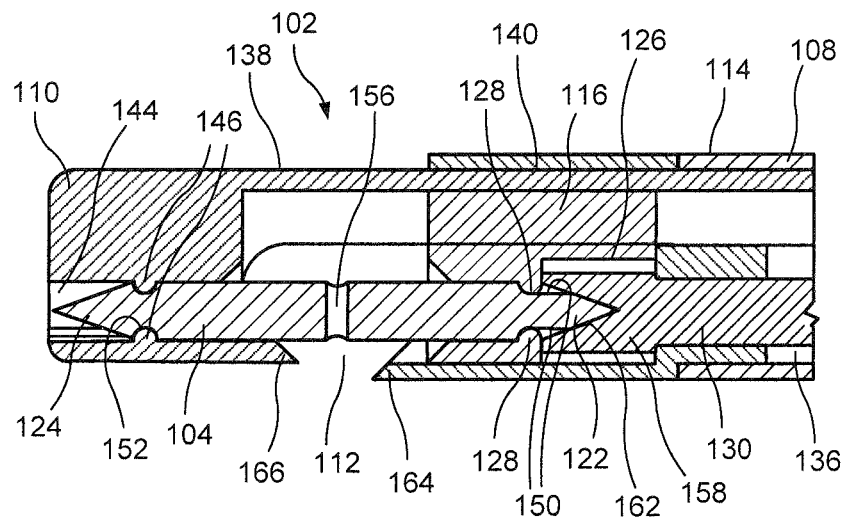
FIG. 7 shows a longitudinal cross-sectional view of the device of FIG. 1, in the closed configuration with the needle locked via a distal locking mechanism.
Figure 8:
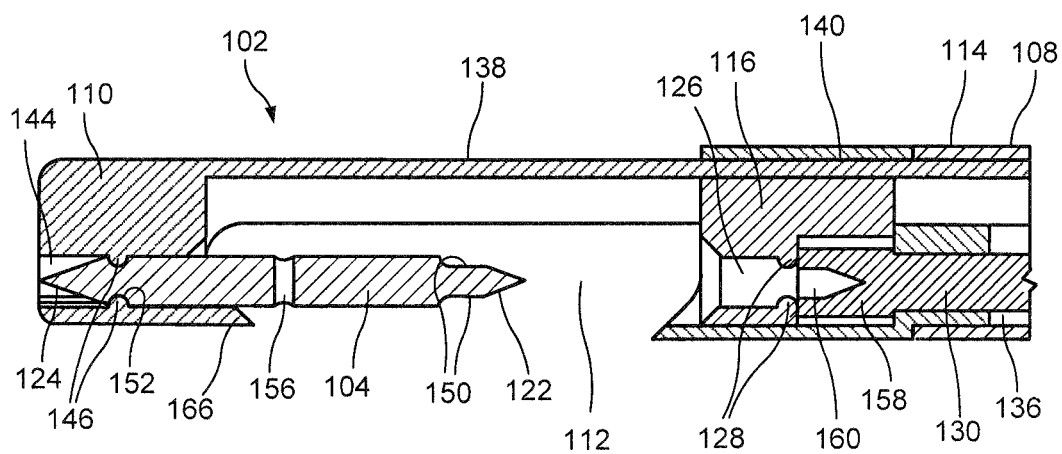
FIG. 8 shows a longitudinal cross-sectional view of the device of FIG. 1, in the open configuration with the needle locked via the distal locking mechanism.
Figure 9:
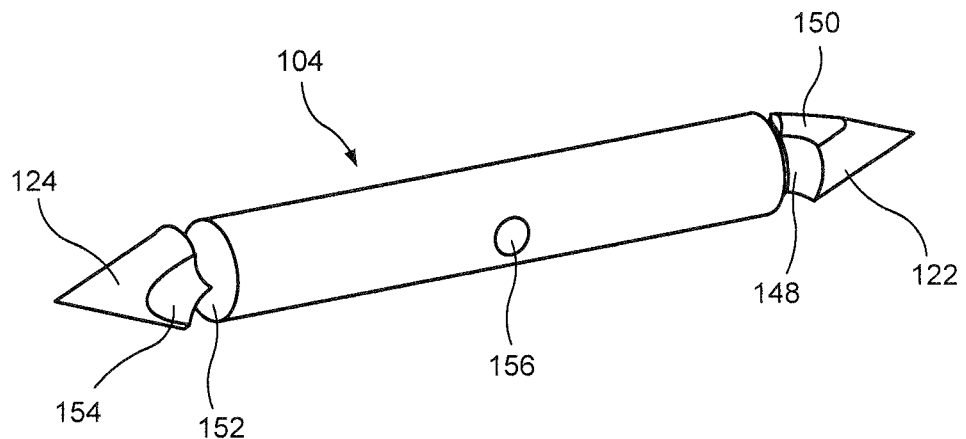
FIG. 9 shows a perspective view of a needle of the device of FIG. 1.
Figure 10:
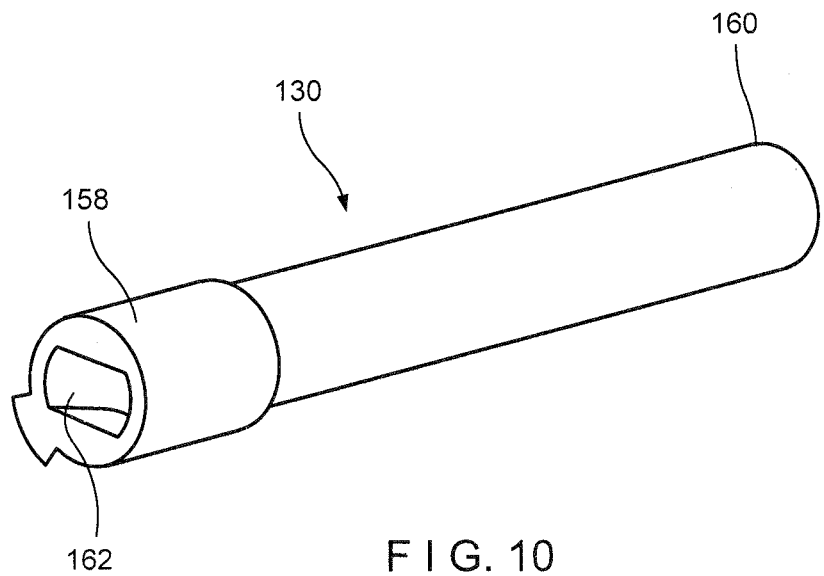
FIG. 10 shows a perspective view of an actuator element of the device of FIG. 1.

As shown in FIGS. 1-10, a tissue closure system 100 according to an exemplary embodiment of the present disclosure comprises a flexible closure device 102 sized and shaped for insertion through an insertion device 170 (e.g., through a working channel of a flexible endoscope) to a target area within a living body to pass a needle 104 and suture 106 through a tissue extending about a periphery 12 of a tissue defect 10 to cinch the tissue defect 10 closed. The closure device 102 includes a longitudinal member 108 and a distal head 110 longitudinally movable relative thereto. A distal end 114 of the longitudinal member 108 includes a proximal head 116 mounted or attached thereto such that target tissue may be received in a space 112 between the distal and proximal heads 110, 116. The needle 104 is passed between the proximal head 116 and the distal head 110 to thread the suture 106 about the periphery of the tissue defect. The proximal head 116 includes a proximal locking mechanism 118 for releasably locking a first end 122 of the needle 104 in a first configuration while the distal head 110 includes a distal locking mechanism 120 for releasably locking a second end 124 of the needle 104 in a second configuration. The needle 104 may be alternately moved between the first and second configurations by rotating the needle 104 about a longitudinal axis thereof, relative to the longitudinal member 108, via an actuating element 130.

In the first configuration, the needle 104 is engaged to the proximal head 116 and may be inserted through the target tissue received within the space 112 by moving the distal head 110 toward the proximal head 116. The proximal movement of the distal head 110 relative to the proximal head 116 pushes the tissue proximally against the needle 104 pushing the needle 104 through the target tissue from a proximal surface of the target tissue to the distal surface. As the distal head 110 is moved toward the proximal head 116, the second end 124 of the needle 104 is received within the distal locking mechanism 120. The needle 104 is then rotated relative to the longitudinal member 108 and the distal head 110, so that the needle 104 is released from the proximal locking mechanism 118 and moved to the second configuration engaging the distal locking mechanism 120. The distal head 110 may then be moved distally relative to the proximal head 116 to draw the suture 106 which is attached to the needle 104, through the target tissue. The closure device 102 may then be repositioned along the periphery of the tissue defect so that an adjacent portion of the target tissue along the periphery of the tissue defect is received within the space 112. The distal head 110 may once again be moved toward the proximal head 116 so that the needle 104 and the suture 106 may be passed through the adjacent portion of the target tissue in a movement which is similar although directed this time from proximal to distal. Once the needle 104 is received again within the proximal locking mechanism 118, the needle 104 is rotated to release the needle 104 from the distal locking mechanism 120 and engage the needle 104 to the proximal locking mechanism 118, moving the closure device 102 to the first configuration. Moving the device 102 to a new position along the periphery of the tissue defect to the next location through which the needle 104 is to be inserted draws the suture 106 through the tissue. This process may be repeated by repositioning the closure device 102 and alternatingly moving the needle 104 between the first and second configurations until the entire periphery of the tissue defect has been threaded via the suture 106. Once the entire periphery of the suture 106 has been threaded through the desired number of locations adjacent to the tissue defect, the needle 104 is released from the closure device 102 to act as an anchor. The suture 106 may then be tensioned to draw edges of the tissue defect together, cinching the tissue defect closed.

The longitudinal member 108 extends longitudinally from a proximal end (not shown) to the distal end 114 and includes a lumen 136 extending therethrough. In one embodiment, the proximal head 116 may be attached or mounted to the distal end 114 of the longitudinal member 108. In another embodiment, the proximal head 116 may be integrally formed therewith. The proximal head 116 includes a slot 126 extending longitudinally therein, the slot 126 sized and shaped to receive the first end 122 of the needle 104. The slot 126 may, for example, extend through an entire length of the proximal head 116. The proximal locking mechanism 118 may be configured as a pair of diametrically opposed protrusions 128 extending laterally into the slot 126 for engaging a portion of the needle 104 in the first configuration. The longitudinal member 108 may also include a longitudinal groove 132 extending along an exterior surface 134 thereof for receiving a portion of the suture 106 therein. The suture 106 may extend along the groove 132.

The distal head 110 is movably coupled to the longitudinal member 108 via a connecting element 138 extending proximally therefrom. The connecting element 138 may be slidably received through an opening 140 extending through the proximal head 116 and through the lumen 136 of the longitudinal member 108 to a proximal end accessible to a user so that the connecting element 138 may be moved longitudinally relative to the longitudinal member 108 to move the distal head 110 toward and away from the proximal head 116. In particular, moving the connecting element 138 distally relative to the longitudinal member 108 moves the distal head 110 distally away from the proximal head 116, increasing the space 112 between the distal and proximal heads 110, 116. Moving the connecting element 138 proximally relative to the longitudinal member 108 draws the distal head 110 proximally toward the proximal head 116, decreasing the space 112 between the distal and proximal heads 110, 116.

Similarly to the proximal head 116, the distal head 110 includes a slot 144 extending longitudinally therein, the slot 144 sized and shaped to receive the second end 124 of the needle 104 therein. The slot 144 according to this embodiment extends, for example, through an entire length of the distal head 110. The distal locking mechanism 120 may be configured as a pair of diametrically opposed protrusions 146 extending laterally into the slot 144 to engage a portion of the needle 104 in the second configuration. The slot 126 in the proximal head 116 and the slot 144 in the distal head 110 may be aligned with one another (e.g., extend coaxially) so that the needle 104 may be alternatingly received and/or locked within the slots 126, 144, as will be described in further detail below. Corresponding opposing protrusions 128, 146 of the proximal and distal heads 116, 110, respectively, may also be aligned with one another. Each of the proximal and distal heads 116, 110 may also include tissue grabbing features such as, for example, teeth 164, 166, respectively, for gripping tissue that is received within the space 112 therebetween.

The needle 104 extends longitudinally from the first end 122 to the second end 124. Each of the first and second ends 122, 124 is tapered so that the ends 122, 124 may pierce tissue as the needle 104 is passed between the proximal and distal heads 116, 110. The needle 104 may also include a hole 156 extending laterally therethrough for attaching the suture 106 to the needle 104. The hole 156 may extend through, for example, a point along a length of the needle 104 equidistant from the first and second ends 122, 124. The hole 156 may, however, extend laterally through any portion of the needle 104 so long as a distal end of the suture 106 may be passed therethrough to attach the suture 106 to the needle 104. In particular, the suture 106 may be passed through the hole 156 and knotted to prevent the distal end of the suture 106 from being disengaged therefrom.

Immediately distal of the tapered first end 122, the needle 104 includes a first circumferential groove 148 extending thereabout. The tapered first end 122, however, also includes a pair of planar surfaces 150 (see FIGS. 7-9) extending therealong, each of the planar surfaces 150 extending on opposite sides of one another along the first end 122 so that the first groove 148 is flush with portions of the first end 122 along which the planar surfaces 150 extend. Thus, in a first position, in which the planar surfaces 150 of the needle 104 are aligned with (e.g., facing toward) the pair of protrusions 128 within the slot 126 of the proximal head 116, the first end 122 of the needle 104 is slidable within the slot 126 as the planar surfaces 150 and the first groove 148 do not engage the protrusions 128. In a second position, however, in which the needle 104 is rotated approximately 90 degrees about a longitudinal axis thereof, the first groove 148 engages the pair of protrusions 128, locking the first end 122 of the needle 104 in the proximal head 116.

Similarly, immediately proximal of the tapered second end 124, the needle 104 includes a second circumferential groove 152 extending thereabout. The tapered second end 124 also includes a pair of planar surfaces 154 extending therealong, each of the planar surfaces 154 extending on opposite sides of one another along the second end 124 so that the second groove 152 is flush with portions of the second end 124 along which the planar surfaces 154 extend. The planar surfaces 154 of the second end 124 may be offset from the planar surfaces 150 of the first end 122 by approximately 90 degrees so that, when the needle is in the first position, as described above, the first end 122 is slidable (e.g., unlocked) within the slot 126 of the proximal head 116, but locked within the slot 142 of the distal head 110. In other words, in the first position, the protrusions 146 of the distal head 110 engage the second groove 152. When the needle 104 is rotated about the longitudinal axis thereof, to the second position, the planar surfaces 154 are moved toward the protrusions 146 so that the second groove 152 disengages the protrusions 146, unlocking the needle 104 with respect to the distal head 110.

Although the exemplary embodiment shows and describes protrusions 128, 146 in the proximal and distal heads 116, 110, respectively, which are aligned with one another and planar surfaces 150, 154 along first and second ends 122, 124 of the needle 104, respectively, that are offset from one another, in another embodiment, the protrusions 128, 146 may be offset while the planar surfaces 150, 154 are aligned. The proximal and distal locking mechanisms 118, 120 may include any of a variety of configurations so long as rotating the needle 104 relative to the longitudinal member 108 moves the closure device 102 between the first and second configurations. For example, in another embodiment, the proximal and distal locking mechanisms may include recesses configured to receive correspondingly shaped protrusions or projections of the needle 104.

The needle 104 may be rotated relative to the longitudinal member 108 via the actuator element 130, which is housed within the lumen 136 of the longitudinal element 108. The actuator element 130 extends longitudinally from a distal end 158 housed within a portion of the proximal head 116 to a proximal end 160, which is connected to a proximal end of the closure device 102 to be accessible to a user of the closure device 102. The distal end 158 includes a recess 162 extending longitudinally thereinto, the recess 162 sized and shaped to receive the first end 122 of the needle 104 therein, when the first end 122 is received within the slot 126 of the proximal head 116. In particular, the first end 122 and the recess 162 are keyed to one another so that, when the first end 122 of the needle 104 is received therein, a rotational movement of the actuator element 130 results in a rotation of the needle 104 relative to the longitudinal member 108.

The closure system 100, as described above, may be used to treat full thickness perforations, in which a perforation or opening 10 exists through all four tissue layers (mucosa, submucosa, muscularis, and serosa), along with perforations that extend through the mucosa and/or submucosa or through any tears or perforations through less than the full thickness of the organ as would be understood by those skilled in the art.

According to a first surgical technique for treating full thickness perforations using the closure system 100, the closure device 102 may be inserted through the insertion device 170 so that the distal head 110 is inserted through the tissue defect 10 to be treated. The closure device 102 may be inserted through the insertion device 170 in the first configuration, so that the needle 104 is engaged to the proximal head 116. The closure device 102 is positioned so that a first target tissue along the periphery 12 of the tissue defect 10 is received between the space 112 between proximal and distal heads 116, 110 of the closure device. Once the first target tissue has been received within the space 112, the proximal and distal heads 116, 110 are moved toward one another so that the second end 124 of the needle 104 pierces the first target tissue received within the space 112 and is received within the slot 144 of the distal head 110. Using the actuator 130, the user rotates the needle 104 to move the closure device 102 to the second configuration, in which the needle 104 is disengaged from the proximal locking mechanism 118 and locked via the distal locking mechanism 120. The needle 104 may be rotated approximately 90 degrees about the longitudinal axis thereof. In one embodiment, rotation of the needle 104 causes the groove 148 adjacent the first end 122 to disengage protrusions 128 within the slot 126 of the proximal head 116 while causing the groove 152 adjacent the second end 124 to engage the protrusions 146 within the slot 144 of the distal head 110. Upon locking the needle 103 to the distal head 110 may be moved distally away from the proximal head 116 so that the needle 104 is passed to a distal side of the first target tissue, thereby threading the suture 106 through the first portion of target tissue.

The closure device 102 may then be positioned along a second target tissue along the periphery 12 of the tissue defect so that the second target tissue is received within the space 112. The second target tissue may, for example, be along a side of the tissue defect opposite the first target tissue. Upon positioning the second target tissue within the space 112, the distal head 110 may then be drawn proximally toward the proximal head 116 so that the first end 122 of the needle 104 pierces the second target tissue and is received within the slot 126 of the proximal head 116. The needle 104 may then be again rotated approximately 90 degrees, via the actuator element 130, so that the needle 104 is moved from the second configuration, in which it is locked via the distal locking mechanism 120, to the first configuration, in which the needle 104 is disengaged from the distal locking mechanism 120 to be locked via the proximal locking mechanism 118. Thus, when the distal head 110 is moved away from the proximal head 116, the needle 104 remains locked to the proximal head 116 so that the needle 104 passes through the second target tissue to a proximal side thereof, thereby threading the suture 106 therethrough.

The above-described steps may be repeated at different locations along the periphery 12 of the tissue defect 10 until the suture 106 has been threaded along a length of the tissue defect 12. In one embodiment, the steps may be alternatingly repeated along opposing sides of the tissue defect 10. It is not required, however, for the suture 106 to be threaded through alternating sides of the tissue defect 10. In another embodiment, the suture 106 may be threaded about the periphery 12 of the tissue defect in a circumferential manner. Once the suture 106 has been threaded along the tissue defect 10, as desired, the needle 104 may be released from either the proximal head 116 to act as an anchor at a position of the last thread. Tensioning of the suture 106 will cause the needle 104 to contact a surface of a portion of tissue along the periphery 10 of the tissue defect 10 to prevent the suture 106 from being unthreaded therefrom and will draw edges of the tissue defect 10 toward one another to close the tissue defect 10. Once the tissue defect 10 has been closed as desired, a cinch (not shown) may be moved along a length of the suture 106 until the cinch contacts a surface of the tissue through which the suture 106 extends. The cinch will hold the tissue defect in the closed position.

According to another embodiment, a method for sealing mucosal layers of tissue may be substantially similar to the full thickness procedure described above. Rather than placing the distal head 110 through a tissue defect to extend distally past a serosa layer of the tissue, the distal head 110 may be placed between the mucosa and submucosa layers of the tissue so that the suture 106 is passed through the mucosa layer in a desired pattern about a perforation to be treated.

According to yet another embodiment, a method for sealing the mucosal and submucal layers of tissue may be substantially similar to the full thickness procedure described above. Rather than inserting the distal head 110 through a tissue defect to extend distally past a last serosa layer of tissue, however, the distal head 110 remains within a lumen of, for example, a GI tract into which the closure device 102 is inserted, at all times. The closure device 102 may be positioned so that a proximal surface of a first target tissue along a tissue defect to be treated is positioned adjacent the space 112. Thus, when the distal head 110 is moved toward the proximal head 116, the distal and proximal heads 110, 116 grip the first target tissue therebetween to from a lump of tissue through which the second end 124 of the needle 104 is pierced. The needle 104 is then rotated to move the needle 104 from the first configuration to the second configuration, locking the needle 104 to the distal head 110 and disengaging the needle 104 from the proximal head 116. The distal head 110 may then be moved away from the proximal head 116, the needle 104 remaining locked to the distal head 110 so that the needle 104 passes through the first target tissue such that the suture 106 is threaded therethrough.

The closure device 102 may then be positioned so that the space 112 is positioned adjacent a proximal surface of a second target tissue along a periphery of a tissue defect to be treated. The second target tissue may extend along a side of the tissue defect opposition the first target tissue. Drawing the distal head 110 toward the proximal head 116 will cause the second target tissue to be gripped between the distal and proximal heads 110, 116 in the form of a lump so that the first end 122 of the needle pierces the second target tissue and is received within the proximal head 116. The needle 104 is then rotated so that the needle 104 is moved from the second configuration to the first configuration, disengaging the distal head 110 to be locked within the proximal head 116. Thus, moving the distal head 110 away from the proximal head 116 causes the needle 110 to be passed through the second target tissue so that the suture 106 is threaded therethrough.

The above-described steps may be repeated at different locations along the periphery of the tissue defect until the suture 106 has been threaded along the tissue defect in a desired pattern. Similarly to the full thickness procedure described above, once the desired suture pattern has been achieved, the needle 104 may be released from the proximal head 116, by rotating the needle 104 relative thereto. The suture 106 is then tensioned so that the needle 104 may act as an anchor while the edges of the tissue defect are drawn together to close the tissue defect. A cinch may be applied over the suture 106 to hold the tissue defect in the closed position.

Although the exemplary methods and procedures describe inserting the closure device 102 to the target area with the needle 104 in the first configuration (i.e., locked to the proximal head 116), the closure device 102 may be similarly inserted to the target area with the needle 104 in the second configuration. The suture 106 will simply initially passed through the target tissue in an opposing direction. The closure device 102 may be otherwise utilized in a similar manner.

Variations may be made in the structure and methodology of the present disclosure, without departing from the spirit and the scope of the disclosure. Thus, it is intended that the present disclosure cover the modifications and variations of this disclosure that may be contemplated by a person of skill in the art.

What is claimed is:

1. A tissue closure device, comprising:
    a needle extending longitudinally from a first end to a second end;
    a suture extending from a distal end attached to the needle to a proximal end extending to a proximal end of the device;
    a proximal head including a proximal slot extending longitudinally therethrough and a proximal locking mechanism for releasably engaging the first end of the needle in the proximal slot in a first configuration; and
    a distal head movably coupled to the proximal head so that the proximal and distal heads are movable relative to one another between an open configuration, in which a target tissue is received therebetween, and a closed configuration, in which the target tissue is gripped therebetween, the distal head including a distal slot extending longitudinally therethrough and a distal locking mechanism for releasably engaging the second end of the needle in the distal slot in a second configuration, the needle movable between the first and second configurations when the proximal and distal heads are in the closed configuration by rotating the needle relative to the proximal and distal heads, the needle alternatingly passed between the proximal and distal heads to thread the suture through the target tissue.

2. The device of claim 1, wherein each of the proximal and distal locking mechanisms includes a pair of diametrically opposed engaging structures.

3. The device of claim 2, wherein the pair of diametrically opposed engaging structures of each of the proximal and distal locking mechanisms are substantially longitudinally aligned with one another.

4. The device of claim 2, wherein the pair of diametrically opposed engaging features include protrusions extending into the proximal and distal slots.

5. The device of claim 1, wherein the first end includes a first groove immediately distal of a tapering thereof and a first pair of planar surfaces extending along a portion of the first end so that the first pair of planar surfaces is flush with the first groove, the first groove engagable with the proximal locking mechanism in the first configuration.

6. The device of claim 5, wherein the second end includes a second groove immediately proximal of a tapering of thereof and a second pair of planar surfaces extending along a portion of the second end so that the second pair of planar surfaces is flush with the second groove, the second groove engagable with the distal locking mechanism in the second configuration.

7. The device of claim 6, wherein the first and second pair of planar surfaces are offset from one another about a longitudinal axis of the needle.

8. The device of claim 1, wherein the distal head and the proximal head are movably coupled to one another via a connecting element extending proximally therefrom to be slidably received within an opening extending longitudinally through the proximal head.

9. The device of claim 1, further comprising an actuating element for rotating the needle between the first and second configurations, the actuating element including a distal end configured to engage the first end of the needle.

* * * * *